US012751838B2

(12) United States Patent
Patnelli et al.

(10) Patent No.: US 12,751,838 B2
(45) Date of Patent: Oct. 6, 2026

(54) ORTHOPAEDIC SURGICAL INSTRUMENT, SYSTEM, AND METHOD FOR INSTALLING A CEMENTLESS FEMORAL STEM COMPONENT IN A DIRECT ANTERIOR APPROACH HIP REPLACEMENT SURGICAL PROCEDURE

(71) Applicant: DePuy Ireland Unlimited Company, Ringaskiddy (IE)

(72) Inventors: Richard A. Patnelli, Batley (GB); James A. Anderson, York (GB); Timothy N. Board, Leeds (GB); J. Bohannon Mason, Charlotte, NC (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 691 days.

(21) Appl. No.: 18/117,071

(22) Filed: Mar. 3, 2023

(65) Prior Publication Data

US 2024/0293238 A1 Sep. 5, 2024

(51) Int. Cl.
*A61F 2/46* (2006.01)
*A61F 2/36* (2006.01)

(52) U.S. Cl.
CPC .......... *A61F 2/4637* (2013.01); *A61F 2/4607* (2013.01); *A61F 2002/365* (2013.01)

(58) Field of Classification Search
CPC .......... A61F 2/4607; A61F 2/36; A61F 2/367; A61F 2/3676; A61F 2002/365; A61F 2002/4681; A61B 17/8841; A61B 17/58; A61B 17/92
See application file for complete search history.

(56) References Cited

U.S. PATENT DOCUMENTS

| | | | |
|---|---|---|---|
| 4,293,962 A | 10/1981 | Fuson | |
| 5,078,746 A | 1/1992 | Garner | |
| 5,383,932 A | 1/1995 | Wilson et al. | |
| 5,972,034 A | 10/1999 | Hofmann et al. | |
| 6,626,913 B1 * | 9/2003 | McKinnon | A61F 2/367 606/86 R |
| 9,737,405 B2 | 8/2017 | Carr et al. | |
| 10,226,294 B2 * | 3/2019 | Li | A61F 2/4609 |

(Continued)

FOREIGN PATENT DOCUMENTS

| | | | |
|---|---|---|---|
| EP | 0379785 A1 | 8/1990 | |
| EP | 0626155 A1 | 11/1994 | |

(Continued)

OTHER PUBLICATIONS

C-STEM AMT Triple Tapered Stabilised Hip, Surgical Technique, 2020, 24 pages.

(Continued)

*Primary Examiner* — Brian A Dukert
(74) *Attorney, Agent, or Firm* — Barnes & Thornburg LLP

(57) ABSTRACT

An orthopaedic surgical system for use in a direct anterior approach orthopaedic surgical hip replacement procedure on a patient's femur includes a stem insertion instrument having an offset locking shaft to install a cementless femoral stem component into a surgically-prepared intramedullary canal of a patient. A method of installing a cementless femoral stem component during performance of a direct anterior approach orthopaedic surgical hip replacement procedure is also disclosed.

18 Claims, 7 Drawing Sheets

(56) References Cited

U.S. PATENT DOCUMENTS

| | | | |
|---|---|---|---|
| 2002/0065518 | A1 | 5/2002 | Naybour et al. |
| 2005/0234462 | A1 | 10/2005 | Hershberger |
| 2008/0172061 | A1 | 7/2008 | Ragbir |
| 2011/0160734 | A1 | 6/2011 | Bastian et al. |
| 2021/0093468 | A1 | 4/2021 | Sweitzer |

FOREIGN PATENT DOCUMENTS

| | | | |
|---|---|---|---|
| EP | 1208821 | A2 | 5/2002 |
| WO | 03065941 | A1 | 8/2003 |
| WO | 2021130372 | A1 | 7/2021 |

OTHER PUBLICATIONS

International Search Report for International Application No. PCT/EP2024/055156, May 8, 2024, 9 pages.

* cited by examiner

ORTHOPAEDIC SURGICAL INSTRUMENT, SYSTEM, AND METHOD FOR INSTALLING A CEMENTLESS FEMORAL STEM COMPONENT IN A DIRECT ANTERIOR APPROACH HIP REPLACEMENT SURGICAL PROCEDURE

TECHNICAL FIELD

The present disclosure relates generally to orthopaedic instruments, and particularly to orthopaedic instruments for use in a direct anterior approach hip replacement surgical procedure.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is installed in the intramedullary canal of the patient's femur and a spherically-shaped head component that bears against the patient's acetabulum or a prosthetic replacement acetabular cup.

Some hip replacement procedures are performed using a direct anterior approach. When using the direct anterior approach, the surgeon does not have line-of-sight access to the intramedullary canal of the patient's femur. This limited access and visibility makes it difficult for the surgeon to install certain components, such as cementless femoral stem components, using instruments designed for other approaches (e.g., a posterior approach).

SUMMARY

According to one aspect, an orthopaedic surgical instrument for implanting a femoral stem component during a direct anterior approach orthopaedic hip replacement surgical procedure on a patient's femur includes a stem insertion instrument. The stem insertion instrument includes an impact plate defining a proximal end of the stem insertion instrument, and a grip extending from a distal end of the impact plate. A longitudinal axis of the grip extends through a center of the impact plate. The grip includes an outer surface that is configured to be gripped during impaction of the impact plate. The stem insertion instrument also includes an elongated body extending from a distal end of the grip, and a locking mechanism captured in the elongated body. The locking mechanism includes a knob that is rotatable relative to the elongated body, and a locking shaft that is secured to a distal surface of the knob and extends through the elongated body such that a threaded distal end of the locking shaft extends outwardly through an opening formed in a distal end of the elongated body. The threaded distal end of the locking shaft is configured to be threadingly received into a threaded bore formed in the femoral stem component. The longitudinal axis of the grip and a longitudinal axis of the locking shaft define an offset angle that is between 10-30 degrees.

In an embodiment, the offset angle defined by the longitudinal axis of the grip and the longitudinal axis of the locking shaft is between 10-20 degrees.

In an illustrative embodiment, the offset angle defined by the longitudinal axis of the grip and the longitudinal axis of the locking shaft is about 12 degrees.

The stem insertion instrument may further include a supplemental extraction plate. The supplemental extraction plate extends medially away from a proximal end of the elongated body, and includes an extraction surface facing toward the distal end of the elongated body that is configured to be impacted during extraction of the femoral stem component.

In an embodiment, rotation of the knob causes rotation of the locking shaft so as to cause its threaded distal end to selectively threadingly engage the threaded bore of the femoral stem component when the threaded distal end of the locking shaft is positioned therein. In such an embodiment, rotation of the knob in a first direction causes the threaded distal end of the locking shaft to threadingly engage the threaded bore of the femoral stem component when the threaded distal end of the locking shaft is positioned therein, whereas rotation of the knob in a direction opposite the first direction causes the threaded distal end of the locking shaft to threadingly disengage the threaded bore of the femoral stem component so as to allow the locking shaft to be removed therefrom.

According to another aspect, an orthopaedic system for use in a direct anterior approach orthopaedic hip replacement surgical procedure on a patient's femur includes an implantable femoral stem component and a stem insertion instrument. The femoral stem component is configured to be implanted into a surgically-prepared intramedullary canal of the patient's femur and includes a longitudinal axis extending in the superior/inferior direction through the femoral stem component, along with an elongated threaded bore having a superior end that opens into a superior surface of the femoral stem component. The stem insertion instrument includes an impact plate defining a proximal end of the stem insertion instrument, and a grip extending from a distal end of the impact plate. A longitudinal axis of the grip extends through a center of the impact plate. The grip also includes an outer surface that is configured to be gripped during impaction of the shaft's impact plate. The stem insertion instrument also includes an elongated body extending from a distal end of the grip, and a locking mechanism captured in the elongated body. The locking mechanism includes a knob that is rotatable relative to the elongated body, and a locking shaft secured to a distal surface of the knob such that a threaded distal end of the locking shaft extends outwardly through an opening formed in a distal end of the elongated body and into the threaded bore of the femoral stem component. When the threaded distal end of the locking shaft of the stem insertion instrument is positioned in the threaded bore of the femoral stem component, the longitudinal axis of the grip and a longitudinal axis of the locking shaft define an offset angle that is between 10-30 degrees, and the longitudinal axis of the grip is coaligned with the longitudinal axis of the femoral stem component.

In an embodiment, when the threaded distal end of the locking shaft of the stem insertion instrument is positioned in the threaded bore of the femoral stem component, the offset angle defined by the longitudinal axis of the grip and the longitudinal axis of the locking shaft is between 10-20 degrees.

In an illustrative embodiment, when the threaded distal end of the locking shaft of the stem insertion instrument is positioned in the threaded bore of the femoral stem component, the offset angle defined by the longitudinal axis of the grip and the longitudinal axis of the locking shaft is about 12 degrees.

In another embodiment, when the threaded distal end of the locking shaft of the stem insertion instrument is positioned in the threaded bore of the femoral stem component, the longitudinal axis of the locking shaft is coaligned with a longitudinal axis of the threaded bore of the femoral stem component.

In an illustrative embodiment, rotation of the knob in a first direction causes the threaded distal end of the locking shaft to threadingly engage the threaded bore of the femoral stem component when the threaded distal end of the locking shaft is positioned therein, whereas rotation of the knob in a direction opposite the first direction causes the threaded distal end of the locking shaft to threadingly disengage the threaded bore of the femoral stem component so as to allow the locking shaft to be removed therefrom.

The stem insertion instrument may also include a supplemental extraction plate that extends medially away from a proximal end of the elongated body. The supplemental extraction plate may include an extraction surface facing toward the femoral stem component when the threaded distal end of the locking shaft of the stem insertion instrument is positioned in the threaded bore of the femoral stem component, with such an extraction surface being configured to be impacted during extraction of the femoral stem component.

According to another aspect, a method of installing a femoral stem component during performance of a direct anterior approach orthopaedic hip replacement surgical procedure on a patient's femur includes surgically-preparing a proximal end of the patient's femur so as to create a resected planar surface. The method also includes threading a threaded distal end of a locking shaft of a stem insertion instrument into a threaded bore formed in the femoral stem component such that a longitudinal axis of a grip of the stem insertion instrument and a longitudinal axis of the threaded bore formed in the femoral stem component define an offset angle that is between 10-30 degrees, and the longitudinal axis of the grip of the stem insertion instrument is coaligned with a longitudinal axis of the femoral stem component. Thereafter, a distal end of the femoral stem component is advanced through the surgically-prepared proximal end of the patient's femur and into an intramedullary canal of the patient's femur. An impact plate on a proximal end of the stem insertion instrument is then impacted so as to implant the femoral stem component into the intramedullary canal of the patient's femur.

The method may also include unthreading the threaded distal end of the locking shaft of the stem insertion instrument from the threaded bore of the femoral stem component subsequent to impacting the impact plate of the stem insertion instrument, and thereafter advancing the stem insertion instrument proximally out of the intramedullary canal of the patient's femur.

In an embodiment, the offset angle defined by the longitudinal axis of the grip of the stem insertion instrument and the longitudinal axis of the threaded bore of the femoral stem component is between 10-20 degrees.

In an illustrative embodiment, the offset angle defined by the longitudinal axis of the grip of the stem insertion instrument and the longitudinal axis of the threaded bore of the femoral stem component is about 12 degrees.

In an embodiment, the threaded distal end of the locking shaft of the stem insertion instrument is threaded into the threaded bore formed in the femoral stem component by rotating a knob secured to the locking shaft so as to rotate the threaded distal end thereof into the threaded bore of the femoral stem component.

In another embodiment, the method includes impacting a supplemental extraction plate that extends medially away from a distal end of the grip of the stem insertion instrument so as to extract the femoral stem component from the intramedullary canal of the patient's femur.

BRIEF DESCRIPTION OF THE DRAWINGS

The detailed description particularly refers to the following figures, in which.

DETAILED DESCRIPTION OF THE DRAWINGS

Figure 1:
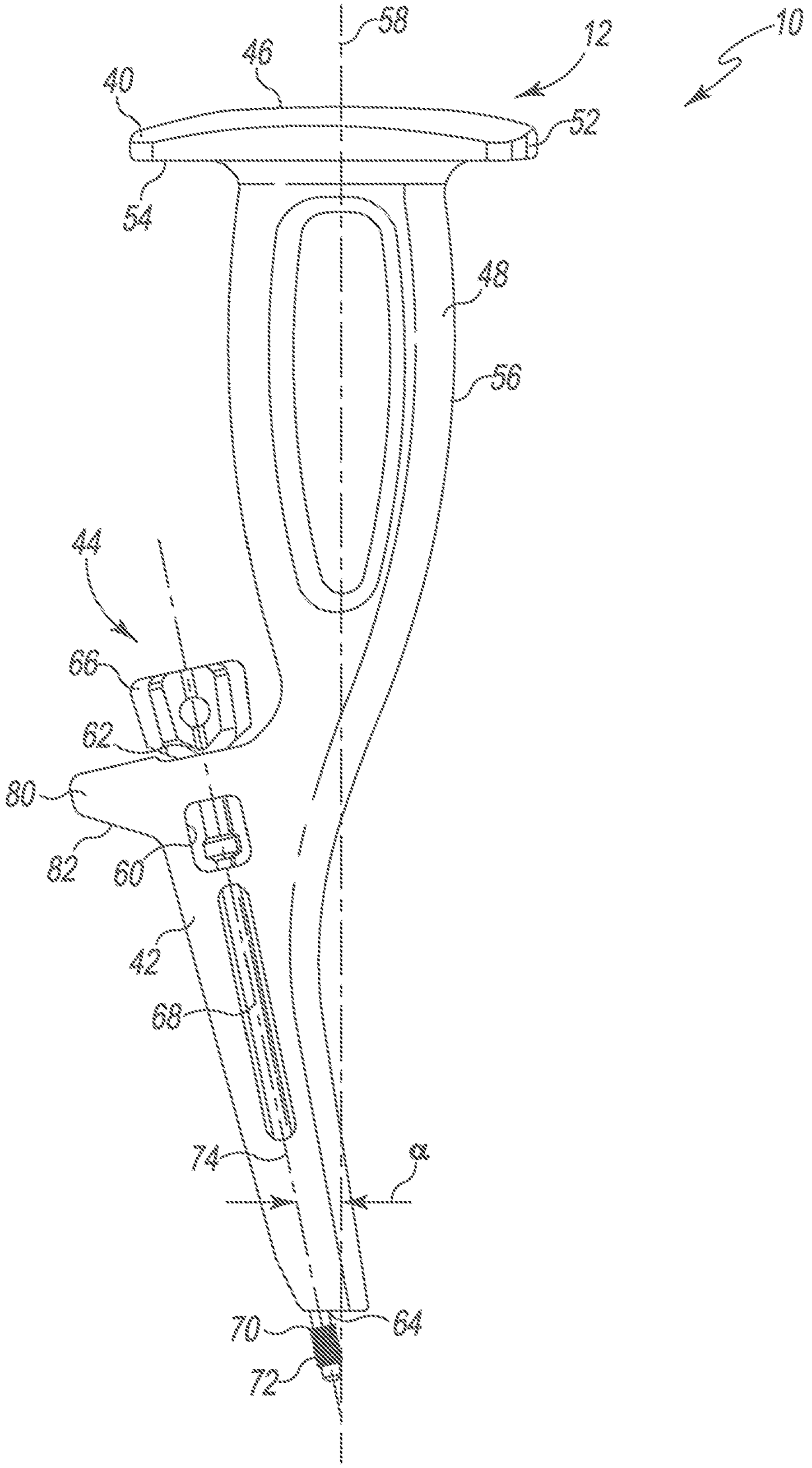
FIG. 1 is a side elevational view of a stem insertion instrument of an orthopaedic surgical system for use in a direct anterior approach orthopaedic surgical hip replacement procedure on a patient's femur.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIGS. 1-4, an orthopaedic surgical system 10 is illustratively embodied to include an insertion instrument 12 and a femoral stem component—specifically, a cementless femoral stem component 14. As will be discussed below in more detail, the insertion instrument 12 is used to install the femoral stem component 14 into an intramedullary canal of a patient's femur during a direct anterior approach hip replacement surgical procedure.

Figure 2:
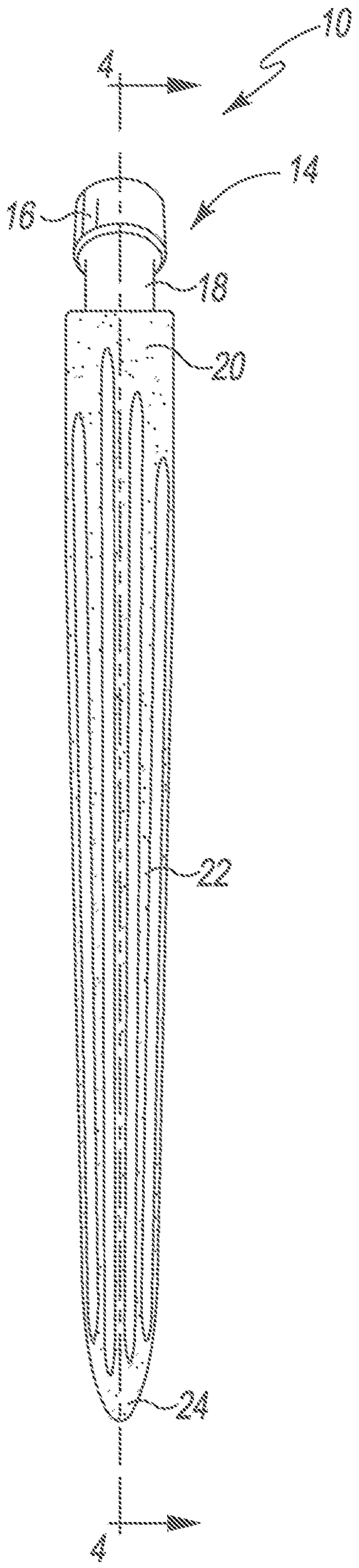
FIGS. 2 and 3 are side elevational views of a cementless femoral stem component.
Figure 3:
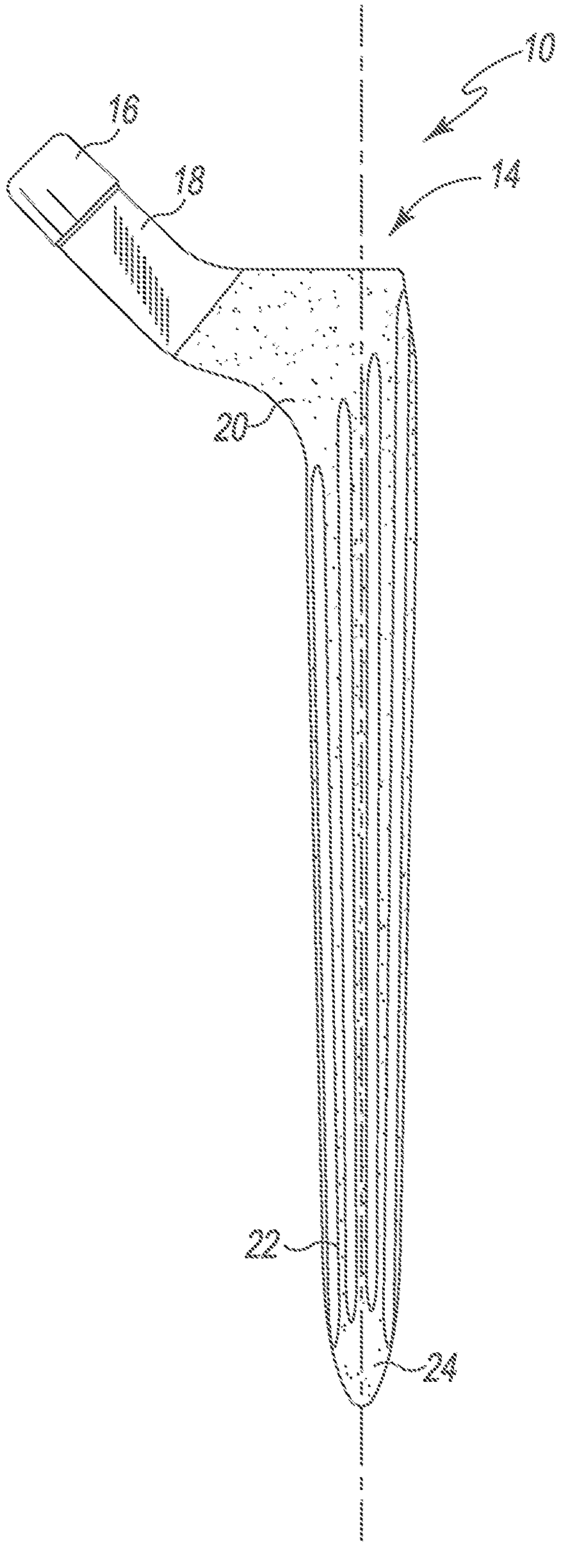
Figure 4:
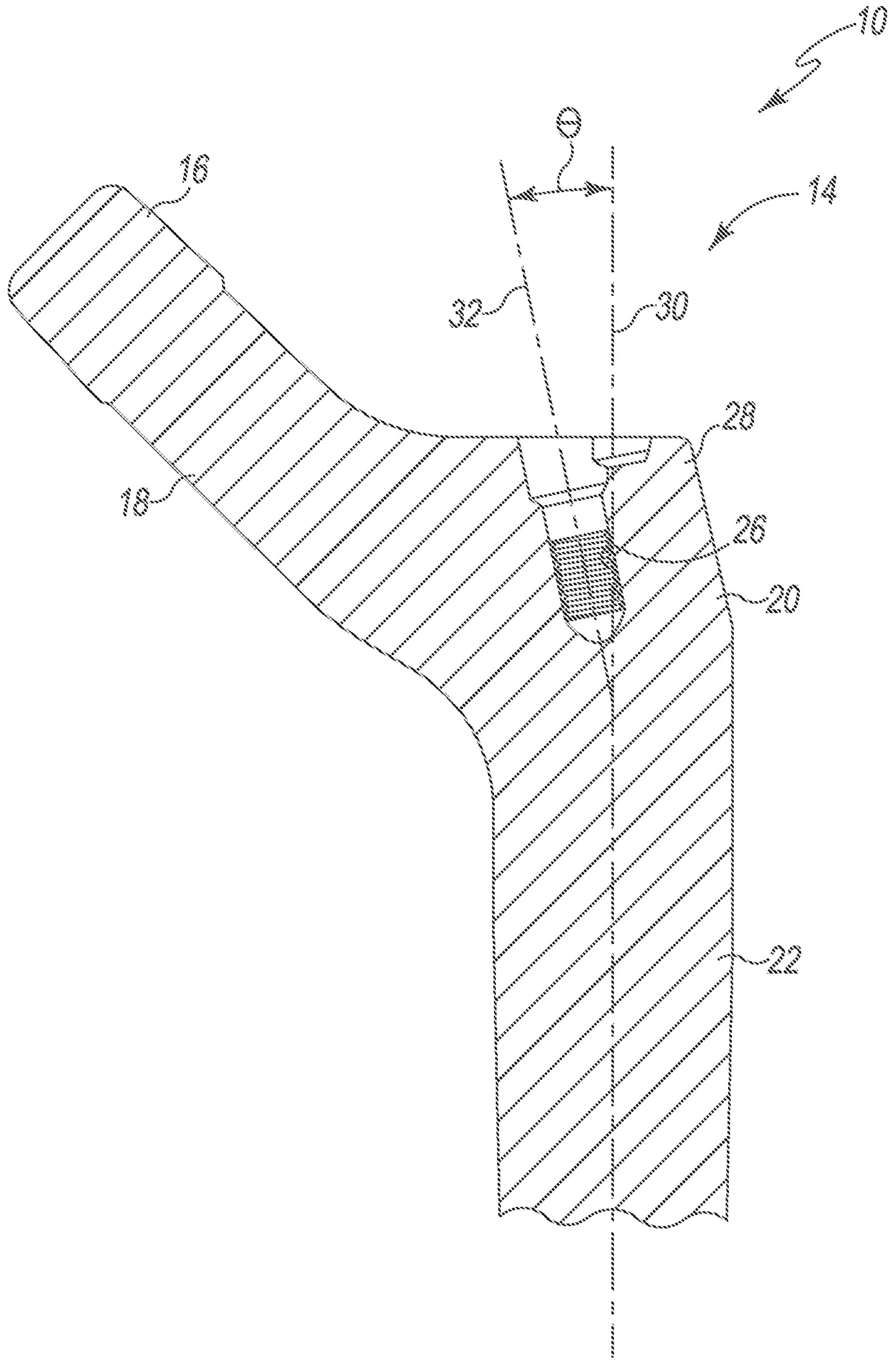
FIG. 4 is a cross sectional view of the cementless femoral stem component of FIGS. 2 and 3 taken along the line 4-4 of FIG. 2, as viewed in the direction of the arrows.
Figure 5:
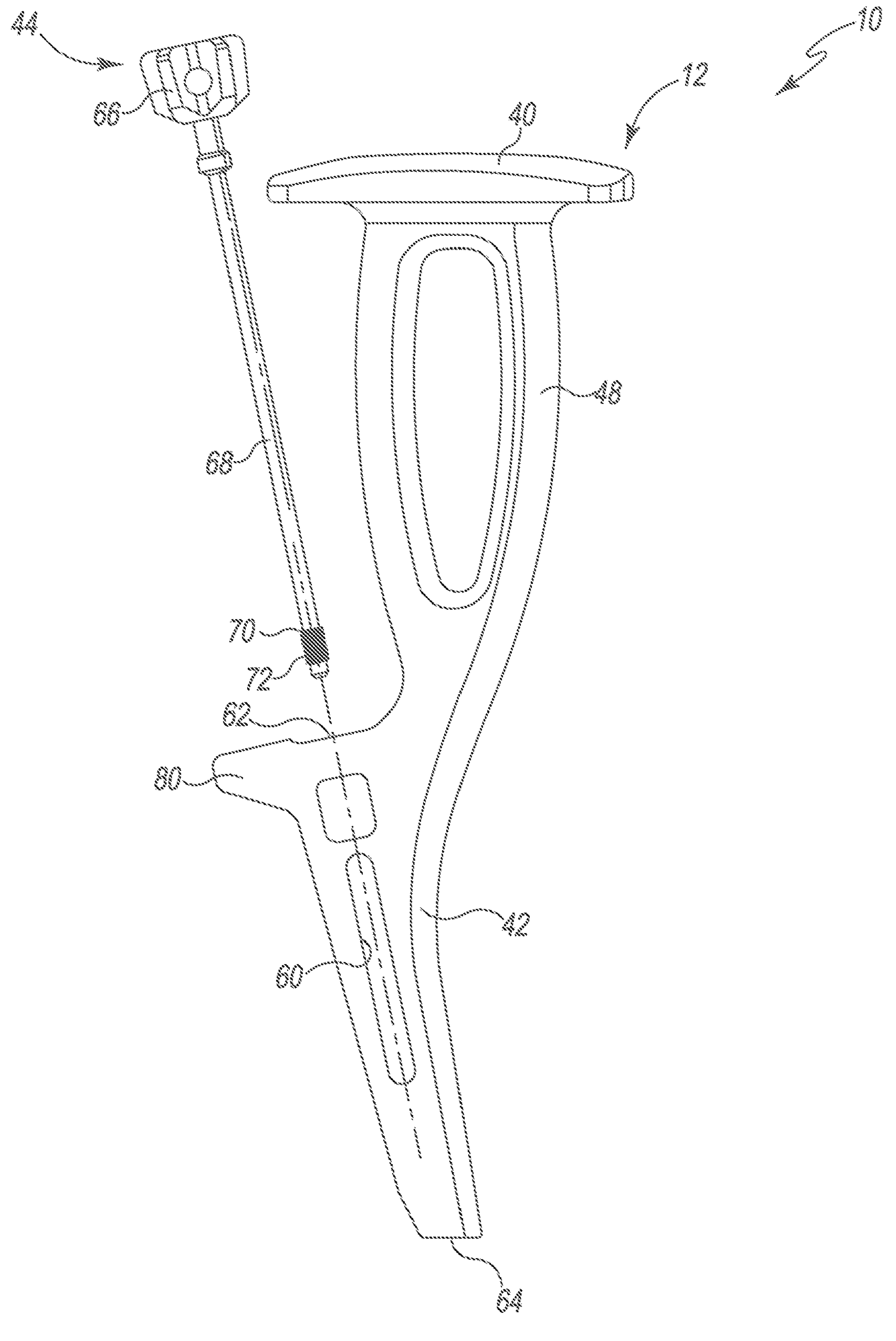
FIG. 5 is a view similar to FIG. 1, but showing the locking mechanism removed from the elongated body of the stem insertion instrument.

As shown in FIGS. 2-4, the femoral stem component 14 is configured to be implanted into the femur 106 of a patient during a hip replacement procedure. In particular, the femoral stem component 14 is implanted into a surgically-prepared (e.g., reamed) intramedullary canal 104 of the patient's femur 106. A femoral head component (not shown) is secured to a trunnion 16 formed in the end of the elongated neck 18 of the femoral stem component 14. When installed on the femoral stem component 14, the femoral head component is positioned to bear on either the patient's natural acetabulum or a prosthetic acetabular component which has been implanted into the patient's pelvis to replace his or her acetabulum. In such a manner, the femoral stem component 14 and the natural or artificial acetabulum collectively function as a system which replaces the natural joint of the patient's hip.

A proximal body 20 defines the midsection of the femoral stem component 14. As such, the elongated neck 18 extends superiorly and medially away from the proximal body 20, with the tapered trunnion 16 being formed in the superior/medial end of the neck 18—i.e., opposite the end that mates with the proximal body 20. A tapered stem 22 extends inferiorly away from the opposite end of the proximal body 20. The tapered stem 20 has a rounded distal end 24 that defines the inferior-most surface of the femoral stem component 14. As can be seen in FIG. 4, a threaded bore 26 is formed in the proximal body's lateral shoulder 28. As will be discussed below in greater detail, the threaded bore 26 threadingly receives the distal tip of a threaded shaft of the insertion instrument 12 during installation of (or removal of) the femoral stem component 14.

In the illustrative embodiment described herein, the femoral stem component 14 is embodied as a cementless femoral stem—i.e., a stem that is installed without the use of bone cement. Moreover, the femoral stem component 14 is embodied as a monolithic metal structure. The femoral stem component 14 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic femoral stem component 14 may also be coated with a surface treatment, such as hydroxyapatite, to enhance biocompatibility. Moreover, the surfaces of the femoral stem component 14 that engage the natural bone, such as the outer surfaces of the proximal body 20 and the tapered stem 22, may be textured to facilitate securing the component to the bone. Such surfaces may also be porous coated to promote bone ingrowth for permanent fixation.

As can be seen in FIG. 4, the threaded bore 26 of the femoral stem component 14 is angled medially. In particular, as can be seen in FIG. 4, the femoral stem component 14 has a longitudinal axis 30 that extends in the superior/inferior direction. While also extending generally in the superior/inferior direction, as can be seen in FIG. 4, the longitudinal axis 32 of the threaded bore 26 is angled medially. Hence, the longitudinal axis 32 of the threaded bore 26 and the longitudinal axis 30 of the femoral stem component 14 define an offset angle θ. In the illustrative embodiment described herein, the offset angle θ of the threaded bore 26 is between 10-30 degrees. In another illustrative embodiment, the offset angle θ of the threaded bore 26 is between 10-20 degrees. In a specific illustrative embodiment, the offset angle θ of the threaded bore 26 is 12 degrees. Such medial offsetting of the threaded bore 26 allows the stem insertion instrument 12 to facilitate the installation of the femoral stem component 14 "around the corner" of the proximal end 108 of a patient's femur 106 despite not having line-of-sight access to the intramedullary canal 104 during a direct anterior approach hip arthroplasty (see FIGS. 7 and 8).

As can be seen in FIG. 1, the insertion instrument 12 has an impact plate 40 on its proximal end. The distal end of an elongated body 42 defines the distal end of the stem insertion instrument 12. A locking mechanism 44 is captured in the instrument's elongated body 42. The locking mechanism 44 is operable to lock the stem insertion instrument 12 to the femoral stem component 14 during implantation of (or removal of) the stem component.

In the exemplary embodiment described herein, the impact plate 40 of the stem insertion instrument 12 includes a rounded metal strike surface 46 formed in the proximal end of the impact plate 40. In use, the surgeon holds the stem insertion instrument 12 via a grip 48 and strikes the strike surface 46 with a surgical mallet, sledge, or other impaction tool to drive the femoral stem component 14 into the surgically-prepared proximal end of the patient's femur (as discussed below in more detail). The impact plate 40 also includes a pair of flanges 52 extending radially outwardly from the center thereof. The flanges 52 serve to protect the surgeon's hand on the grip 48 during impaction. Moreover, the flanges 52 can be impacted from their underside surface 54 if the stem insertion instrument 12 is used to extract a femoral stem component 14.

As can be seen in FIG. 1, the grip 48 extends distally from the distal end of the impact plate 40. The grip 48 includes outer surfaces 56 that are sized and shaped to be gripped by the surgeon during impaction of the instrument's impact plate 40. As can be seen in FIG. 1, the longitudinal axis 58 of the grip 48 passes through the center of the impact plate 40. In such a way, the surgeon can utilize the grip 48 to accurately center the impact plate 40 during impaction. As can also be seen in FIG. 1, the elongated body 42 extends distally away from the distal end of the grip 48. The elongated body 42 has a bore 60 extending therethrough. Specifically, the bore 60 extends between an opening 62 formed in the proximal end of the elongated body 42 and an opening 64 formed in the opposite, distal end of the elongated body 42.

The locking mechanism 44 includes a knob 66 that is rotatable relative to the elongated body 42 and a locking shaft 68 that is secured to a distal surface of the knob 66. The locking shaft 68 extends away from the knob 66 and includes a threaded distal end 70. The threaded distal end 70 is sized and shaped to threadingly engage the threaded bore 26 of the femoral stem component 14 so as to selectively lock the insertion instrument 12 to the femoral stem component 14. Specifically, the distal end 70 of the locking shaft 68 has a set of locking threads 72 defined therein. The locking threads 72 are configured to threadingly engage the threaded bore 26 of the femoral stem component 14 so as to secure the insertion instrument 12 to the femoral stem component 14.

The locking mechanism 44 may be removably captured in, or otherwise secured to, the elongated body 42 of the stem insertion instrument 12. Specifically, the threaded distal end 70 of the locking shaft 68 may be advanced into the proximal opening 62 of the elongated body 42 and thereafter advanced through the elongated body's bore 60 and out through the distal opening 64. Due to the diameter of the knob 66 being larger than the proximal opening 62 of the elongated body 42, the knob 66 acts as a stop during installation of the locking shaft 68 into the elongated body's bore 60. When the knob 66 is positioned proximate to the proximal end of the elongated body 42, the threaded distal end 70 of the locking shaft 68 extends outwardly through the body's distal opening 64 and into the threaded bore 26 of the femoral stem component 14. When a surgeon or other user rotates the knob 66, the locking shaft's threads 72 are likewise rotated. Rotation in one direction (e.g., clockwise) may be used to tighten, and hence secure, the stem insertion instrument 12 to the femoral stem component 14, with rotation in the opposite direction (e.g., counterclockwise) being used to loosen, and hence, uncouple the stem insertion instrument 12 from the femoral component 14.

Figure 6:
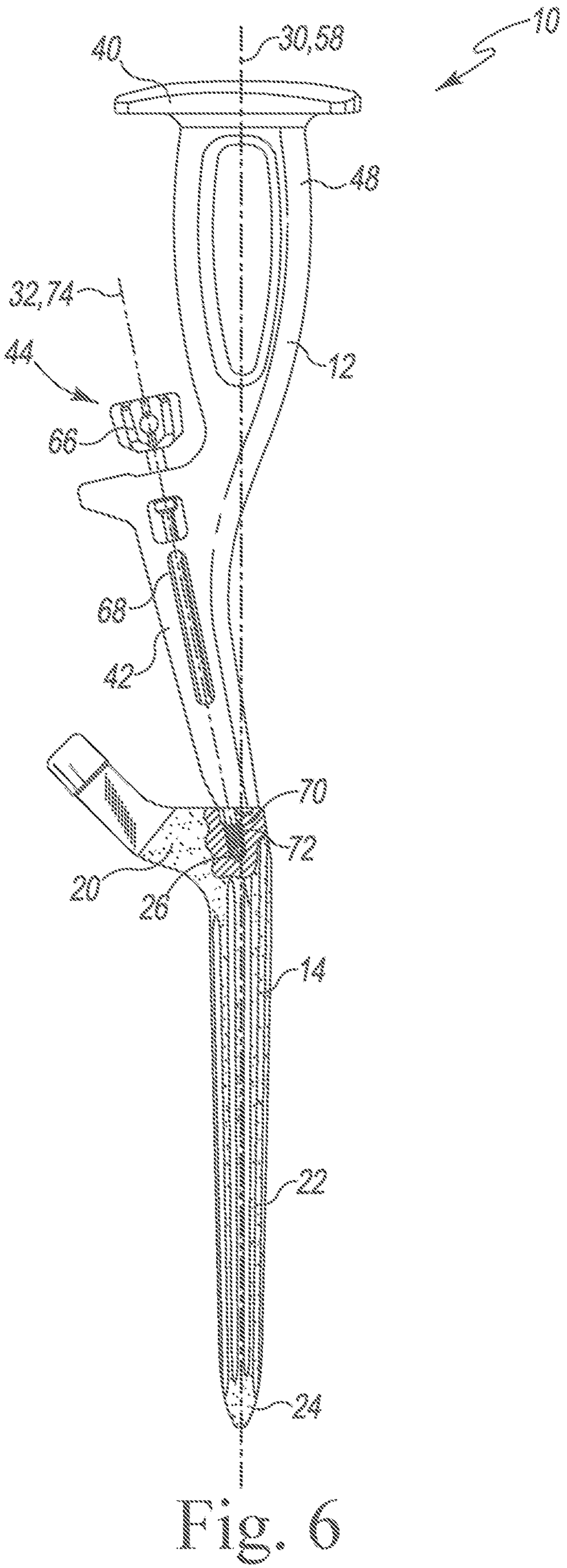
FIG. 6 is a side elevational view showing the stem insertion instrument of FIG. 1 secured to the femoral stem component of FIGS. 2-4, note a portion of the proximal end of the femoral stem component has been cut away for clarity of description.

As can be seen in FIGS. 1 and 6, the elongated body's bore 60, and hence the locking mechanism 44 captured therein, of the stem insertion instrument 12 is angled medially. In particular, as discussed above and can be seen in FIG. 1, the longitudinal axis 58 of the grip 48 extends in the superior/inferior direction and passes through the center of the impact plate 40. While also extending generally in the superior/inferior direction, as can be seen in FIG. 1, the longitudinal axis 74 of the locking shaft 68 is angled medially. Hence, the longitudinal axis 58 of the grip 48 and the longitudinal axis 74 of the locking shaft 68 define an offset angle $\alpha$. The offset angle $\alpha$ of the locking shaft 68 matches the offset angle $\theta$ of the threaded bore 26. Hence, in the illustrative embodiment described herein, the offset angle $\alpha$ of the locking shaft 68 is between 10-30 degrees. In another illustrative embodiment, the offset angle $\alpha$ of the locking shaft 68 is between 10-20 degrees. In a specific illustrative embodiment, the offset angle $\alpha$ of the locking shaft 68 is 12 degrees. Such medial offsetting of the locking shaft 68 allows the shaft 68 to be positioned in alignment with the threaded bore 26 of the femoral stem component 14. In other words, as shown in FIG. 6, when the stem insertion instrument 12 is secured to the femoral stem component 14, the longitudinal axis 74 of the locking shaft 68 is coaligned with the longitudinal axis 32 of the threaded bore 26 of the femoral stem component 14. Such an arrangement also aligns the grip 48 and the femoral stem component 14. In particular, as shown in FIG. 6, when the stem insertion instrument 12 is secured to the femoral stem component 14, the longitudinal axis 58 of the grip 48 and the longitudinal axis 30 of the femoral stem component 14 are coaligned with one another. As such, a relatively high impact load transfer efficiency (i.e., impact load transfer efficiency=output force/input force) is achieved since strike forces are transferred along a common axis despite the angled locking connection between the femoral stem component 14 and the instrument 12.

As can be seen in FIGS. 1 and 6, the stem insertion instrument 12 also includes supplemental extraction plate 80. The supplemental extraction plate 80 extends medially away from the proximal end of the elongated body 42. The supplemental extraction plate 80 includes an extraction surface 82 that faces toward the distal end of the elongated body 42 (i.e., toward the stem component 14 when the stem component is secured to the stem insertion instrument 12). The extraction surface 82 is configured to be impacted with a surgical mallet, sledge, or other impaction tool to drive the femoral stem component 14 out of the surgically-prepared proximal end of the patient's femur during extraction of the femoral stem component 14. The use of the supplemental extraction plate 80 is particularly useful during an anterior surgical approach since the underside surfaces 54 of the flanges 52 of the impact plate 40 can occasionally be close to, or actually in contact with, soft tissue. Thus, the supplemental extraction plate 80 provides an alternative strike surface to use in lieu of the impact plate 40 in such circumstances.

As can be seen in FIGS. 1 and 5-8, the lateral side of the stem insertion instrument 12 is curved inwardly (i.e., curved medially). Specifically, the lateral side of the grip 48 and the elongated body 42 cooperate to define an arcuate-shaped, concave surface that curves medially toward the opposite (i.e., medial) side of the insertion instrument 12. Such a configuration provides clearance during use of the stem insertion instrument 12. In particular, during a direct anterior approach hip arthroplasty, use of an insertion instrument with a relatively straight lateral side may result in impingement of the instrument on the greater trochanter of the patient's femur 106. In the case of the insertion instrument 12, the curved lateral surface provides clearance of the greater trochanter as the surgeon advances the assembled femoral stem component 14 and the stem insertion instrument 12 around the greater trochanter and into the proximal end 108 of the patient's femur 106.

In the illustrative embodiment, the stem insertion instrument 12 is formed from a metallic material such as, for example, stainless steel. In particular, the impact plate 40, the grip 48, the elongated body 42, and the locking mechanism 44 form an assembled metallic instrument. The stem insertion instrument 12 may be formed by conventional machining techniques, or alternatively, by the use of 3-D printing technology. In the case of 3-D printing, the stem insertion instrument 12 is formed in a layer-by-layer fashion.

In use, the orthopaedic surgical system 10 may be used by a surgeon to install the femoral stem component 14 in the intramedullary canal 104 of a patient's femur 106 during a direct anterior approach hip replacement surgical procedure. Prior to installation of the femoral stem component 14, the surgeon performs a number of pre-operative and intra-operative surgical steps to prepare the patient's femur 106 to receive the femoral stem component 14. For example, the surgeon uses a bone saw to surgically resect the patient's natural femoral head and create a surgically-prepared proximal end 108 of the patient's femur 106 that includes, amongst other features, a resected planar surface 102. The surgeon also assembles and installs a number of trial components and trials the fit and function of the components to be installed before implanting the femoral stem component 14.

The surgeon then selects a femoral stem component 14 having the desired size from the various available sizes. The surgeon then installs the stem insertion instrument 12 to the selected femoral stem component 14. To do so, the surgeon first installs the locking mechanism 44 in the elongated body 42 of the insertion instrument 12 by advancing the threaded distal end 70 of the locking shaft 68 into the proximal opening 62 of the elongated body 42 and through the elongated body's bore 60 such that the threaded distal end 72 of the locking shaft 68 extends through the body's distal opening 64. Thereafter, the surgeon inserts the threaded distal end 72 of the locking shaft 68 into the threaded bore 26 of the selected femoral stem component 14. The surgeon or other user then rotates the knob 66, and hence the locking shaft's threads 72, in a direction (e.g., clockwise) to tighten, and hence secure, the stem insertion instrument 12 to the femoral stem component 14, as shown in FIG. 6.

Figure 7:
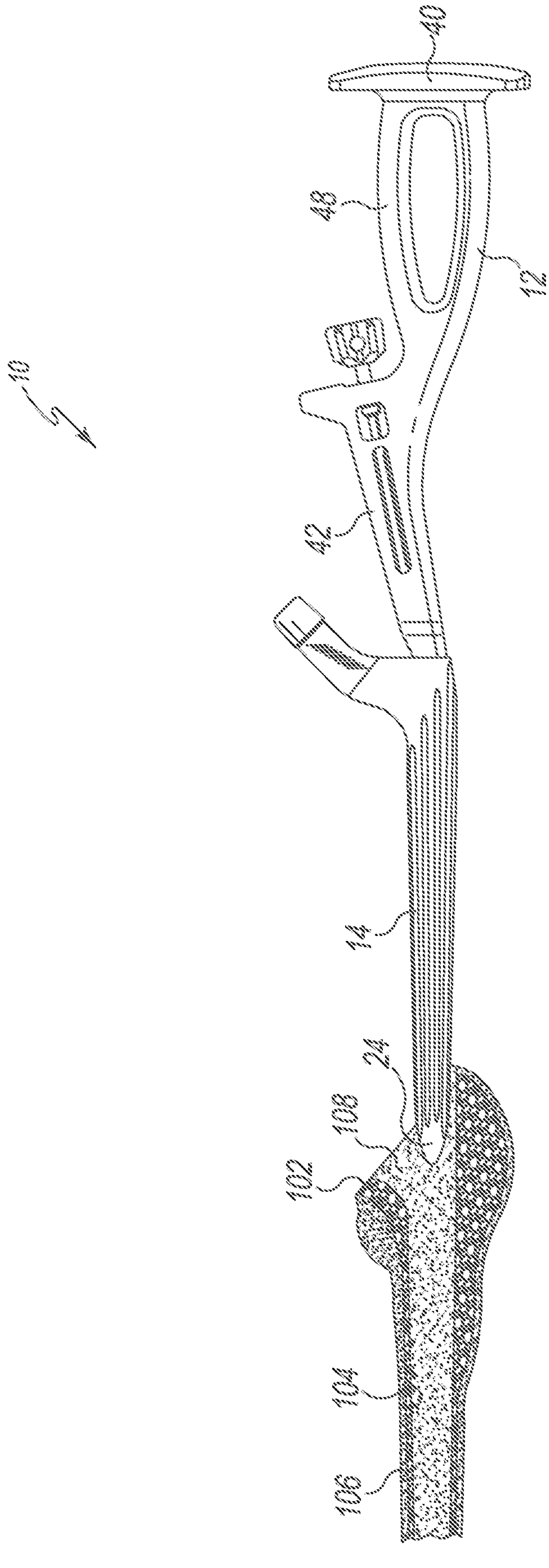
FIG. 7 is a cross-sectional view of a patient's femur during a direct anterior approach hip replacement surgical procedure, showing a surgeon introducing the femoral stem component of FIGS. 2-4 by use of the stem insertion instrument of FIG. 1.

Once the insertion instrument 12 is secured to the femoral stem component 14, as shown in FIG. 7, the surgeon advances the distal end 24 of the femoral stem component 14 through the surgically-prepared proximal end 108 of the patient's femur 106 and into the intramedullary canal 104.

The surgeon grips the grip 48 and urges it distally toward the surgically-prepared proximal end 108 of the patient's femur 106. Doing so advances the femoral stem component 14 distally and thus further into the intramedullary canal 104 of the patient's femur 106. As shown in FIG. 7, during such advancement of the femoral stem component 14, the configuration of the curved lateral side of the insertion instrument 12 facilitates the surgeon's advancement of the femoral stem component 14 by providing clearance of the greater trochanter of the patient's femur 106.

Figure 8:
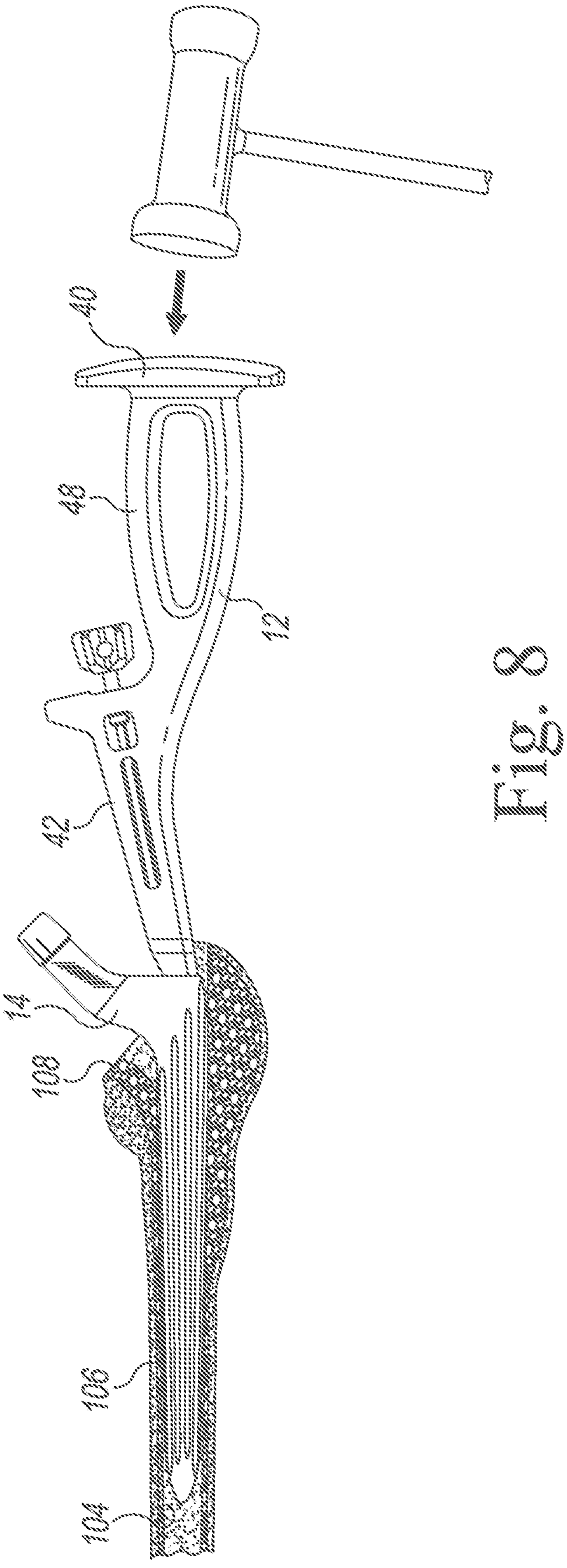
FIG. 8 is a view similar to FIG. 7, but showing the femoral stem component being impacted into the bone tissue of the intramedullary canal of the patient's femur.

The surgeon continues to advance the grip 48 (and hence the femoral stem component 14) distally into the intramedullary canal 104 of the patient's femur 106 until the stem component 14 engages bone tissue thereby providing a tactile indication to the surgeon that the femoral stem component 14 has reached the desired initial depth. As shown in FIG. 8, once the femoral stem component 14 is positioned in such a manner, the surgeon strikes the impact plate 40 of the stem insertion instrument 12 with a surgical mallet, sledge, or other impaction tool to drive the femoral stem component 14 into the bone tissue until the stem component 14 is fully seated in the intramedullary canal 104 of the patient's femur 106.

Once the femoral stem component 14 has been impacted to the desired depth, the surgeon then assesses if the femoral stem component 14 is properly positioned in the intramedullary canal 104. If the surgeon is satisfied with the fit of the femoral stem component 14 within the intramedullary canal 104, the surgeon rotates the knob 66 of the locking mechanism in a direction (e.g., counterclockwise) to loosen, and hence, uncouple the stem insertion instrument 12 from the implanted femoral stem component 14. The surgeon then pulls or otherwise urges the grip 48 in a direction away from the implanted femoral stem component 14 thereby releasing the threaded distal end 72 of the instrument's locking shaft 68 from the stem component's threaded bore 26. Once released in such a manner, the surgeon removes the insertion instrument 12 from the surgically-prepared proximal end 108 of the patient's femur. Thereafter, the surgeon performs the remaining steps in the surgical procedure.

If the surgeon determines that the femoral stem component 14 needs to be removed and/or repositioned, the surgeon may use the impact plate 40 and/or the supplemental extraction plate 80 to do so. Specifically, with the stem insertion instrument 12 secured to the implanted femoral stem component 14 (or re-secured to the stem component 14 if the insertion instrument 12 had been previously removed from it), the surgeon may impact the underside surfaces 54 of the flanges 52 of the impact plate 40 with a surgical mallet, sledge, or other impaction tool to drive the femoral stem component 14 out of engagement with the bone tissue of the intramedullary canal 104 of the patient's femur 106. Moreover, if the underside surfaces 54 of the flanges 52 of the impact plate 40 are positioned close to, or actually in contact with, soft tissue, the surgeon may instead use the supplemental extraction plate 80. To do so, the surgeon impacts the plate's extraction surface 82 with a surgical mallet, sledge, or other impaction tool to drive the femoral stem component 14 out of engagement with the bone tissue of the intramedullary canal 104 of the patient's femur 106. Once the surgeon has extracted the femoral stem component 14 by use of the impact plate 40 and/or the supplemental extraction plate 80, the surgeon may use the stem insertion instrument 12 to re-install the femoral stem component 14 in a desired orientation in the manner described above.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument for implanting a femoral stem component during a direct anterior approach orthopaedic hip replacement surgical procedure on a patient's femur, comprising:
- a stem insertion instrument comprising:
  - an impact plate defining a proximal end of the stem insertion instrument,
  - a grip extending from a distal end of the impact plate, wherein (i) a longitudinal axis of the grip extends through a center of the impact plate, and (ii) the grip comprises an outer surface that is configured to be gripped during impaction of the impact plate,
  - an elongated body extending from a distal end of the grip, and
  - a locking mechanism captured in the elongated body, the locking mechanism comprising (i) a knob that is rotatable relative to the elongated body, and (ii) a locking shaft secured to a distal surface of the knob and extending through the elongated body such that a threaded distal end of the locking shaft extends outwardly through an opening formed in a distal end of the elongated body, the threaded distal end of the locking shaft being configured to be threadingly received into a threaded bore formed in the femoral stem component,
  - wherein the longitudinal axis of the grip and a longitudinal axis of the locking shaft define an offset angle that is between 10-30 degrees.

2. The orthopaedic surgical instrument of claim 1, wherein the offset angle defined by the longitudinal axis of the grip and the longitudinal axis of the locking shaft is between 10-20 degrees.

3. The orthopaedic surgical instrument of claim 1, wherein the offset angle defined by the longitudinal axis of the grip and the longitudinal axis of the locking shaft is about 12 degrees.

4. The orthopaedic surgical instrument of claim 1, wherein the stem insertion instrument further comprises a supplemental extraction plate, wherein:
- the supplemental extraction plate extends medially away from a proximal end of the elongated body, and
- the supplemental extraction plate comprises an extraction surface facing toward the distal end of the elongated body that is configured to be impacted during extraction of the femoral stem component.

5. The orthopaedic surgical instrument of claim 1, wherein rotation of the knob causes rotation of the locking shaft so as to cause its threaded distal end to selectively threadingly engage the threaded bore of the femoral stem component when the threaded distal end of the locking shaft is positioned therein.

6. The orthopaedic surgical instrument of claim 5, wherein:

rotation of the knob in a first direction causes the threaded distal end of the locking shaft to threadingly engage the threaded bore of the femoral stem component when the threaded distal end of the locking shaft is positioned therein, and rotation of the knob in a direction opposite the first direction causes the threaded distal end of the locking shaft to threadingly disengage the threaded bore of the femoral stem component so as to allow the locking shaft to be removed therefrom.

7. An orthopaedic system for use in a direct anterior approach orthopaedic hip replacement surgical procedure on a patient's femur, comprising an implantable femoral stem component configured to be implanted into a surgically-prepared intramedullary canal of the patient's femur, the femoral stem component comprising (i) a longitudinal axis extending in the superior/inferior direction through the femoral stem component, and (ii) an elongated threaded bore having a superior end that opens into a superior surface of the femoral stem component, and a stem insertion instrument comprising: (i) an impact plate defining a proximal end of the stem insertion instrument, (ii) a grip extending from a distal end of the impact plate, wherein (a) a longitudinal axis of the grip extends through a center of the impact plate, and (b) the grip comprises an outer surface that is configured to be gripped during impaction of the shaft's impact plate, (iii) an elongated body extending from a distal end of the grip, and (iv) a locking mechanism captured in the elongated body, the locking mechanism comprising (a) a knob that is rotatable relative to the elongated body, and (b) a locking shaft secured to a distal surface of the knob such that a threaded distal end of the locking shaft extends outwardly through an opening formed in a distal end of the elongated body and into the threaded bore of the femoral stem component, wherein, when the threaded distal end of the locking shaft of the stem insertion instrument is positioned in the threaded bore of the femoral stem component: (i) the longitudinal axis of the grip and a longitudinal axis of the locking shaft define an offset angle that is between 10-30 degrees, and (ii) the longitudinal axis of the grip is coaligned with the longitudinal axis of the femoral stem component.

8. The orthopaedic system of claim 7, wherein, when the threaded distal end of the locking shaft of the stem insertion instrument is positioned in the threaded bore of the femoral stem component, the offset angle defined by the longitudinal axis of the grip and the longitudinal axis of the locking shaft is between 10-20 degrees.

9. The orthopaedic system of claim 7, wherein, when the threaded distal end of the locking shaft of the stem insertion instrument is positioned in the threaded bore of the femoral stem component, the offset angle defined by the longitudinal axis of the grip and the longitudinal axis of the locking shaft is about 12 degrees.

10. The orthopaedic system of claim 7, wherein, when the threaded distal end of the locking shaft of the stem insertion instrument is positioned in the threaded bore of the femoral stem component, the longitudinal axis of the locking shaft is coaligned with a longitudinal axis of the threaded bore of the femoral stem component.

11. The orthopaedic system of claim 7, wherein:

rotation of the knob in a first direction causes the threaded distal end of the locking shaft to threadingly engage the threaded bore of the femoral stem component when the threaded distal end of the locking shaft is positioned therein, and rotation of the knob in a direction opposite the first direction causes the threaded distal end of the locking shaft to threadingly disengage the threaded bore of the femoral stem component so as to allow the locking shaft to be removed therefrom.

12. The orthopaedic system of claim 7, wherein the stem insertion instrument further comprises a supplemental extraction plate, wherein:

the supplemental extraction plate extends medially away from a proximal end of the elongated body, the supplemental extraction plate comprises an extraction surface facing toward the femoral stem component when the threaded distal end of the locking shaft of the stem insertion instrument is positioned in the threaded bore of the femoral stem component, and the extraction surface is configured to be impacted during extraction of the femoral stem component.

13. A method of installing a femoral stem component during performance of a direct anterior approach orthopaedic hip replacement surgical procedure on a patient's femur, comprising:

surgically-preparing a proximal end of the patient's femur so as to create a resected planar surface, threading a threaded distal end of a locking shaft of a stem insertion instrument into a threaded bore formed in the femoral stem component such that (i) a longitudinal axis of a grip of the stem insertion instrument and a longitudinal axis of the threaded bore formed in the femoral stem component define an offset angle that is between 10-30 degrees, and (ii) the longitudinal axis of the grip of the stem insertion instrument is coaligned with a longitudinal axis of the femoral stem component, advancing a distal end of the femoral stem component through the surgically-prepared proximal end of the patient's femur and into an intramedullary canal of the patient's femur, and impacting an impact plate on a proximal end of the stem insertion instrument so as to implant the femoral stem component into the intramedullary canal of the patient's femur.

14. The method of claim 13, further comprising:

unthreading the threaded distal end of the locking shaft of the stem insertion instrument from the threaded bore of the femoral stem component subsequent to impacting the impact plate of the stem insertion instrument, and advancing the stem insertion instrument proximally out of the intramedullary canal of the patient's femur.

15. The method of claim 13, wherein threading the threaded distal end of the locking shaft of the stem insertion instrument into the threaded bore formed in the femoral stem component comprises threading the threaded distal end of the locking shaft of the stem insertion instrument into the threaded bore formed in the femoral stem component such that the offset angle defined by the longitudinal axis of the grip of the stem insertion instrument and the longitudinal axis of the threaded bore of the femoral stem component is between 10-20 degrees.

16. The method of claim 13, wherein threading the threaded distal end of the locking shaft of the stem insertion instrument into the threaded bore formed in the femoral stem component comprises threading the threaded distal end of the locking shaft of the stem insertion instrument into the threaded bore formed in the femoral stem component such that the offset angle defined by the longitudinal axis of the grip of the stem insertion instrument and the longitudinal axis of the threaded bore of the femoral stem component is about 12 degrees.

17. The method of claim 13, wherein threading the threaded distal end of the locking shaft of the stem insertion instrument into the threaded bore formed in the femoral stem component comprises rotating a knob secured to the locking shaft so as to rotate the threaded distal end thereof into the threaded bore of the femoral stem component.

18. The method of claim 13, further comprising impacting a supplemental extraction plate that extends medially away from a distal end of the grip of the stem insertion instrument so as to extract the femoral stem component from the intramedullary canal of the patient's femur.

* * * * *